(12) United States Patent
Doerr et al.

(10) Patent No.: US 11,707,295 B2
(45) Date of Patent: Jul. 25, 2023

(54) MEDICAL INSTRUMENT AND ASSOCIATED METHOD

(71) Applicant: KARL STORZ Endovision, Inc., Charlton, MA (US)

(72) Inventors: Daniel Glenn Doerr, Orlando, FL (US); Roland Strelitzki, Altamonte Springs, FL (US); Gary Wayne Haberland, Winter Park, FL (US); John A. Farnella, Orlando, FL (US)

(73) Assignee: KARL STORZ SE & CO KG

( * ) Notice: Subject to any disclaimer, the term of this patent is extended or adjusted under 35 U.S.C. 154(b) by 26 days.

(21) Appl. No.: 16/266,980

(22) Filed: Feb. 4, 2019

(65) Prior Publication Data

US 2019/0216497 A1   Jul. 18, 2019

Related U.S. Application Data

(62) Division of application No. 14/938,619, filed on Nov. 11, 2015, now abandoned.

(51) Int. Cl.
*A61B 17/34* (2006.01)
*A61B 17/00* (2006.01)

(52) U.S. Cl.
CPC ...... *A61B 17/3421* (2013.01); *A61B 17/3417* (2013.01); *A61B 17/3423* (2013.01); *A61B 17/3439* (2013.01); *A61B 17/3474* (2013.01); *A61B 17/3478* (2013.01); *A61B 17/3496* (2013.01); *A61B 2017/0042* (2013.01); *A61B 2017/00477* (2013.01); *A61B 2017/347* (2013.01); *A61B 2017/3445* (2013.01); *A61B 2017/3466* (2013.01); *A61B 2017/3484* (2013.01)

(58) Field of Classification Search
CPC ........ A61B 2017/3445; A61B 17/3423; A61B 2017/347
See application file for complete search history.

(56) References Cited

U.S. PATENT DOCUMENTS

2009/0216196 A1* 8/2009 Drontle ................. A61B 17/24
 604/164.01
2009/0281498 A1* 11/2009 Acosta ............... A61B 17/3421
 604/164.01

* cited by examiner

*Primary Examiner* — Tasnim Mehjabin Ahmed
(74) *Attorney, Agent, or Firm* — David N. Villalpando

(57) ABSTRACT

A medical instrument includes a handle, a trocar in communication with the handle, and a cannula in communication with the trocar and the handle. The cannula is engaged (locked) with the handle when linearly displaced proximally towards the handle and, the cannula is disengaged (unlocked) from the handle when linearly displaced distally away from the handle. The cannula is linearly reciprocated, between the locked position and the unlocked position, along a linear travel path defined parallel to a longitudinal axis of the trocar such that the cannula is prohibited and permitted to articulate about the longitudinal axis of the trocar, and relative to the handle, respectively. Advantageously, the cannula is locked and unlocked from the trocar by without requiring an external force exerted generally transverse to trocar and/or cannula—thereby permitting a user to lock/unlock the cannula, relative to the trocar, with one hand.

18 Claims, 15 Drawing Sheets

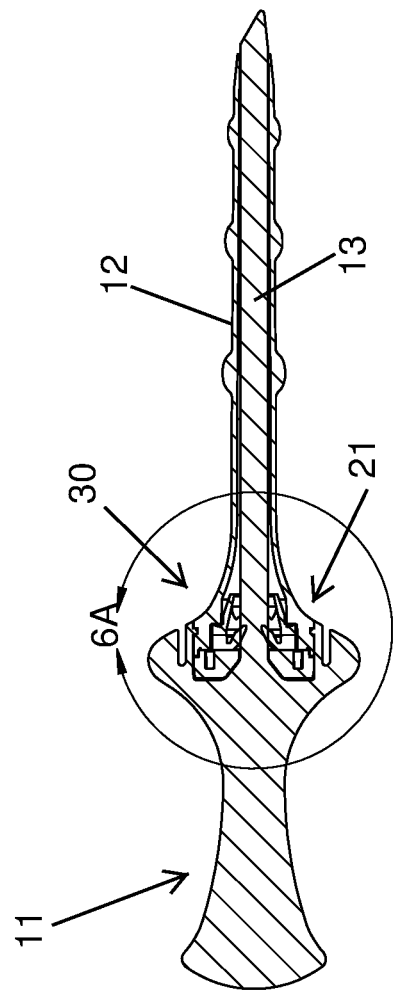
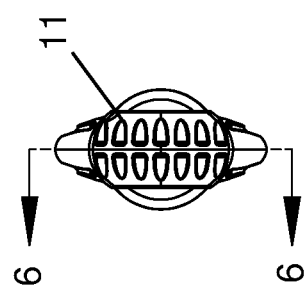
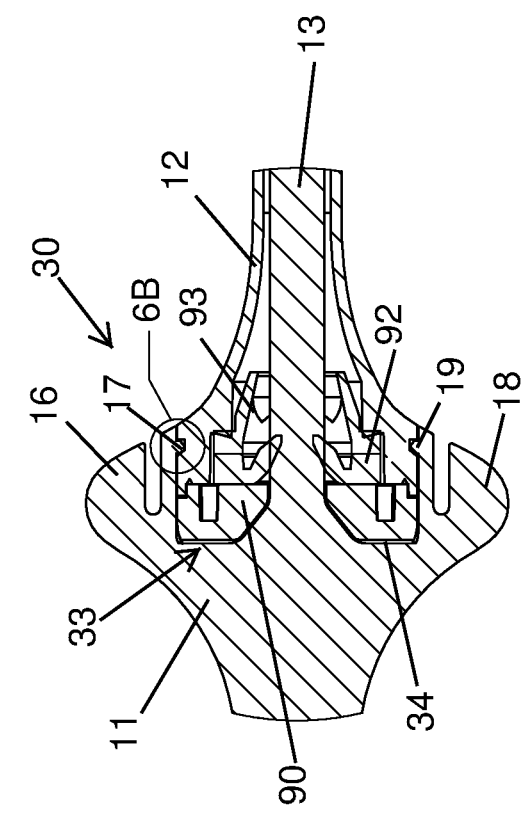
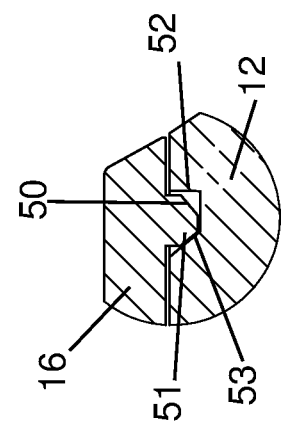
FIG. 5
FIG. 6
FIG. 6A
FIG. 6B

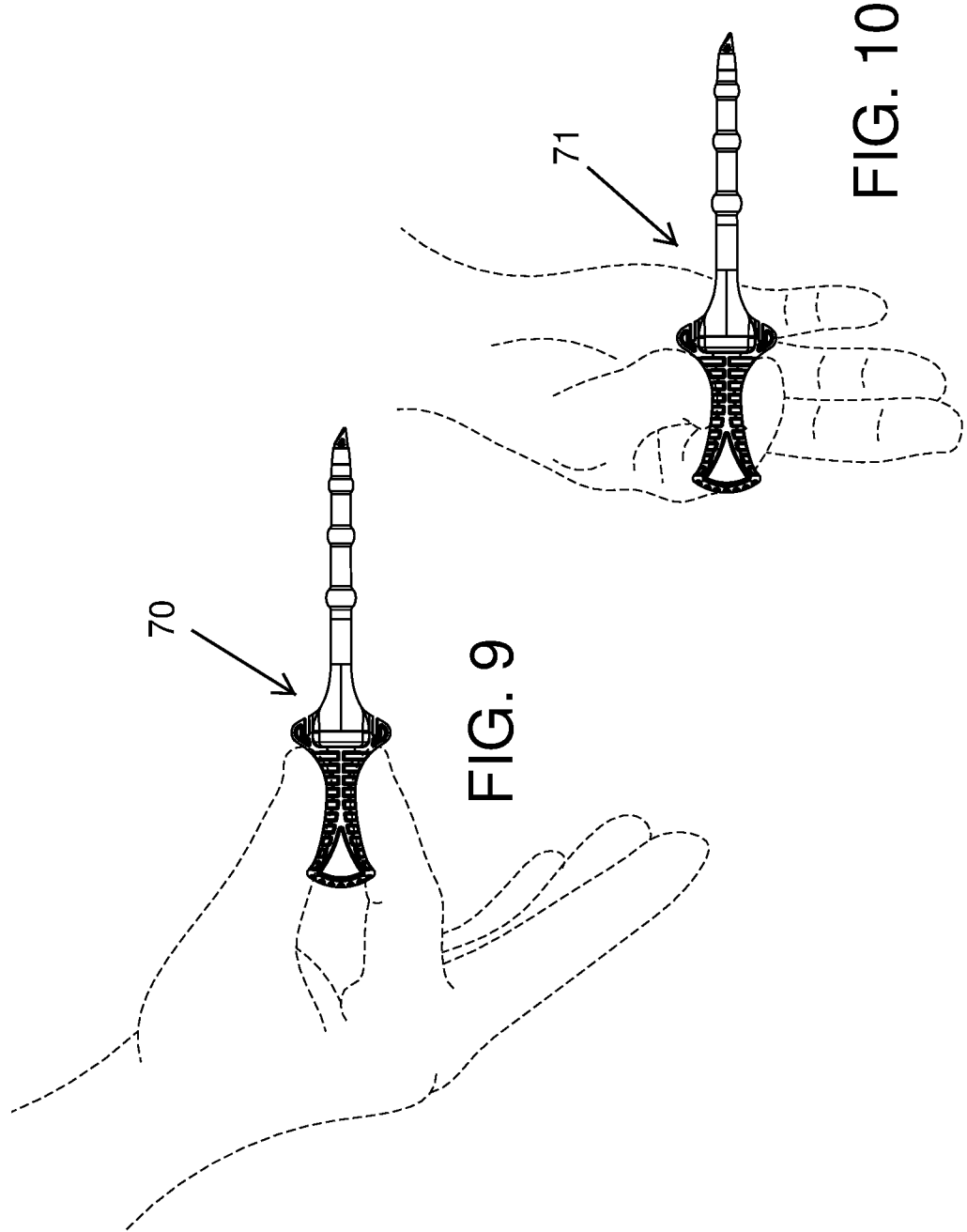

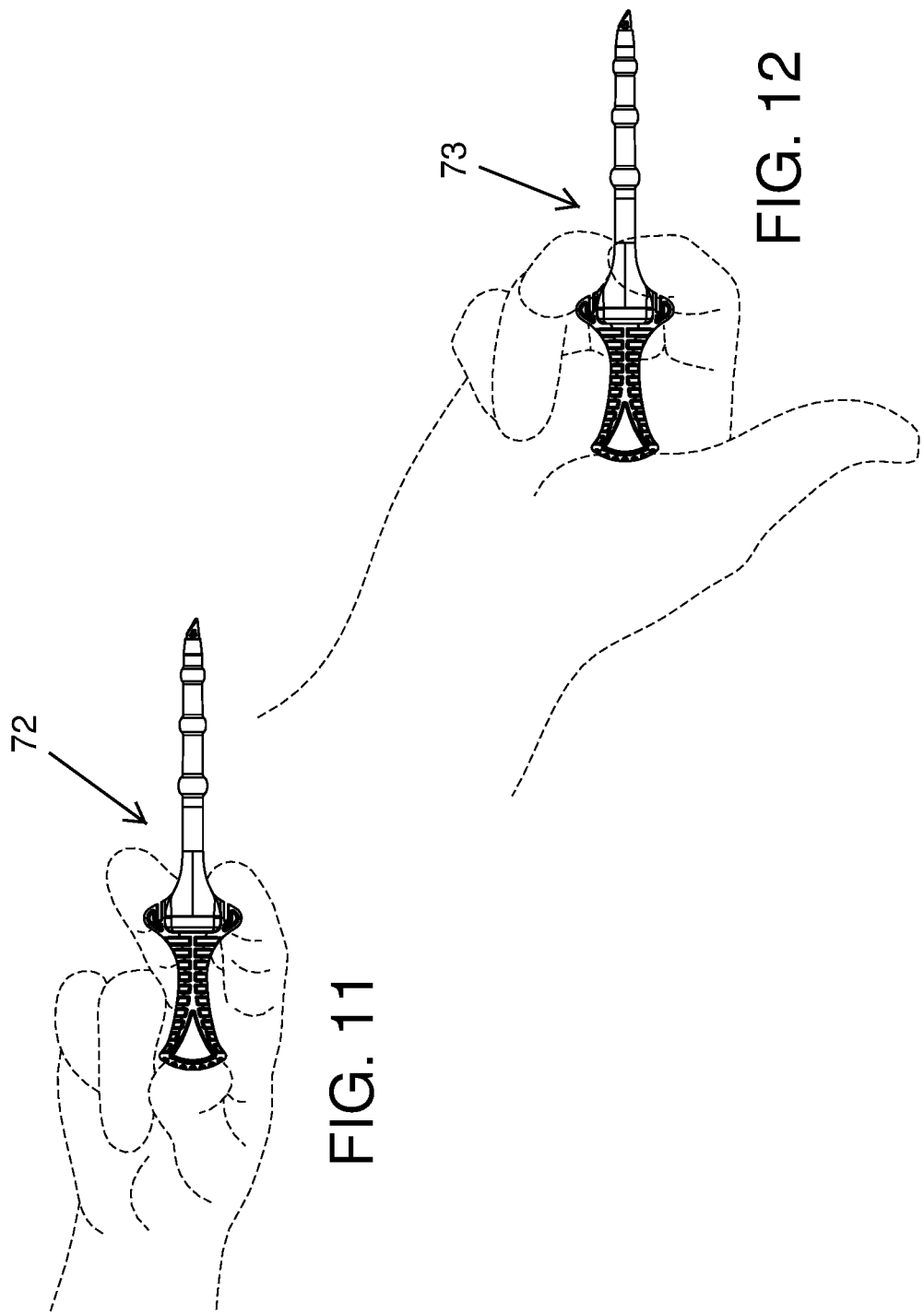

MEDICAL INSTRUMENT AND ASSOCIATED METHOD

CROSS REFERENCE TO RELATED APPLICATIONS

This is a divisional application of U.S. patent application Ser. No. 14/938,619, filed Nov. 11, 2015 and currently pending, the entire disclosure of which is incorporated by reference herein.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to small trocars and, more particularly, to a low profile, small cannula system employing fewer components, an ergonomic locking mechanism, cannula retention features, and a low profile multi-grip handle for reducing manufacturing costs, minimizing undesirable movement during surgery, and facilitating desired manipulation of the cannula system.

Prior Art

Surgical access systems such as low profile, small cannula systems facilitate minimally invasive surgery across a body wall and within a body cavity. With such low profile, small cannulae systems, the diameter of the cannula is typically less than approximately 5 mm. For example, in abdominal surgery, small cannulae provide a working channel across the abdominal wall to facilitate the use of instruments within the abdominal cavity. Low profile cannulae systems typically include a small-diameter cannula, which provides the working channel, and a low profile trocar that is used to place the cannula across a body wall, such as the abdominal wall. As an example, the trocar is inserted into the working channel of the cannula and pushed through the body wall with a penetration force of sufficient magnitude to result in penetration of the body wall.

Unfortunately, conventional low profile, small cannula systems suffer from high costs because the precision and desired features often require nine to fourteen components, thereby driving up manufacturing costs. For example, a locking mechanism is employed to secure the trocar to the cannulae for preventing undesirable rotation and translation of the trocar relative to the cannula. Conventional locking mechanisms require two hands to unlock the trocar from the cannula. For example, a first external force generally transverse to the trocar length is exerted at the locking mechanism, while a second external force parallel to the cannula length urges the cannula away from the trocar. Such simultaneous first and second external forces are cumbersome for the practitioner.

Additionally, low profile, small cannula systems are often used during pediatric cases, where the abdominal walls are not as fully formed as a normal adult patient. The outer surface of the cannula associated with a trocar is generally smooth. The smoothness of a cannula surface makes placement of the cannula through a body wall relatively easy and safe. However, a smooth cannula may not have the desired retention characteristics once the cannula has been placed through a body wall. This smoothness and ease of placement may present problems as instruments and specimens are removed from a body cavity through the cannula and the associated seal systems of the trocar. It is highly desirable for a cannula to remain fixed in an appropriate position once placed.

Conventional cannulae systems also often include an obtrusive valve and/or insufflation port valve. Such valves and/or ports are generally integrated with the cannula housing positioned at the proximal end of the cannula. The valves and/or ports are positioned in communication with the cannula and/or trocar for selectively controlling the passage of an insufflation fluid, e.g. carbon dioxide, through flexible tubing into a portion of the cannula and/or trocar. However, current valves and/or ports are positioned in a manner that obstructs use and/or manipulation of the cannula system (e.g., handle grip), especially when two or more cannula systems are employed adjacent to and/or in contact with other. Obstruction based upon the positioning of valves and/or ports on a cannula system often causes a doctor to place his or her hands in a compromised or undesirable position. In addition, current valves and/or ports are prone to accidental manipulation during procedures. Accidental manipulation is a common occurrence that results in desufflation of the body cavity and can lead to frustrating and even dangerous situations as the medical professional's field of view is compromised.

Accordingly, a need remains for a low profile, small cannula system in order to overcome at least one aforementioned shortcoming. The exemplary embodiment(s) satisfy such a need by providing a low profile, small cannula system employing fewer components, an ergonomic locking mechanism, cannula retention features, and a low profile multi-grip handle that is convenient and easy to use, lightweight yet durable in design, versatile in its applications, and designed for reducing manufacturing costs, minimizing undesirable movement during surgery, and facilitating desired manipulation of the cannula system.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a low profile, small cannula system employing fewer components, an ergonomic locking mechanism, cannula retention features, and a low profile multi-grip handle for reducing manufacturing costs, minimizing undesirable movement during surgery, and facilitating desired manipulation of the cannula system. These and other objects, features, and advantages of the non-limiting exemplary embodiment(s) are provided by a medical instrument for use during a medical procedure. Such a medical instrument includes a handle, a trocar in static communication with the handle, and a cannula in dynamic communication with the trocar and the handle. Notably, the cannula is engaged with the handle when linearly displaced proximally towards the handle and, conversely, the cannula is disengaged from the handle when linearly displaced distally away from the handle.

Advantageously, the cannula is at a locked position when linearly engaged with the handle and the cannula is at an unlocked position when linearly disengaged from the handle. In this manner, the cannula is linearly reciprocated, between the locked position and the unlocked position, along a linear travel path defined parallel to a longitudinal axis of the trocar such that the cannula is prohibited and permitted to articulate about the longitudinal axis of the trocar, and relative to the handle, respectively. Advantageously, the cannula is locked and unlocked from the trocar by without requiring an external force exerted generally transverse to trocar and/or cannula—thereby permitting a user to lock/unlock the cannula, relative to the trocar, with one hand.

In a non-limiting exemplary embodiment, the handle includes a distal end including a first locking flange having a first male member extending towards the linear travel path, and a second locking flange having a second male member spaced from the first male member and extending towards the linear travel path. Notably, the cannula is engaged and disengaged from each of the first male member and the second male member as the cannula is linearly reciprocated along the linear travel path towards and away from the distal end of the handle, respectively. Again, no second external force generally transverse to the trocar and/or cannula is needed to lock/unlock the cannula. The user can perform such locking/unlocking functions with merely one hand.

In a non-limiting exemplary embodiment, the cannula is caused to simultaneously engage and disengage each of the first male member and the second male member when the cannula is linearly displaced between the locked position and the unlocked position, respectively.

In a non-limiting exemplary embodiment, the cannula includes a proximal end including a perimeter outer wall having a first female member and a second female member spaced therefrom. Such first female member and second female member are aligned with the first male member and the second male member, respectively, when the proximal end of the cannula is linearly introduced, along the longitudinal axis, into the distal end of the handle. In this manner, the first male member and the second male member are operably received and retained within the first female member and the second female member, respectively, as the proximal end of the cannula is linearly intercalated between the first locking flange and the second locking flange.

In a non-limiting exemplary embodiment, each of the first locking flange and the second locking flange is caused to resiliently articulate along mutually exclusive arcuate paths, respectively, away from and towards the linear travel path as the cannula is linearly reciprocated between the locked position and the unlocked position, respectively.

In a non-limiting exemplary embodiment, the handle further includes an inner wall extending from the first male member to the second male member, and at least one rib intermediately disposed between the first male member and the second male member. The at least one rib is statically engaged with the inner wall of the trocar. Notably, the cannula further includes at least one mating slot selectively engaged and disengaged with the at least one rib when the cannula is linearly reciprocated, along the linear travel path, between the locked position and the unlocked position.

In a non-limiting exemplary embodiment, the at least one rib is linearly inserted and retracted from the at least one mating slot so that the cannula is prohibited and permitted to rotating about the longitudinal axis of the trocar, and relative to the handle, when the cannula is registered at the locked position and the unlocked position, respectively.

In a non-limiting exemplary embodiment, the proximal end of the cannula has a proximal wall linearly engaged and disengaged from the inner wall of the handle when cannula is linearly reciprocated, along the longitudinal axis, between the locked positon and the unlocked position, respectively.

In a non-limiting exemplary embodiment, at least one of the first male member and the second male member includes a first engaging edge and a first disengaging edge. Furthermore, at least one of the first female member and the second female member includes a second engaging edge and a second disengaging edge. In this manner, when the at least one of the first male member and the second male member is seated within a corresponding one of the first female member and the second female member, the first disengaging edge lays substantially parallel to the second disengaging edge and thereby maintains frictional contact therewith while the first engaging edge lays non-parallel to the second engaging edge.

In a non-limiting exemplary embodiment, at least one of the handle and the cannula includes an insufflation port for introducing gas along the linear travel path.

The present disclosure further includes a method for utilizing a medical instrument during a medical procedure. Such a method includes the steps of: providing a handle; providing a trocar in static communication with the handle; providing and dynamically communicating a cannula with the trocar and the handle; linearly engaging the cannula, at a locked position, with the handle by linearly displacing the cannula proximally towards the handle; linearly disengaging the cannula, to an unlocked position, from the handle by linearly displacing the cannula distally away from the handle; and prohibiting and permitting the cannula to articulate about the longitudinal axis of the trocar, and relative to the handle, respectively, by linearly reciprocating the cannula, between the locked position and the unlocked position, along a linear travel path defined parallel to a longitudinal axis of the trocar.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 5 is a rear elevational view of the medical instrument illustrated in FIG. 1;

FIG. 6 is a cross-sectional view taken along line 6-6 in FIG. 5;

FIG. 6A is an enlarged view of section 6A identified in FIG. 6;

FIG. 6B is an enlarged view of section 6B identified in FIG. 6;

FIG. 9 is a side elevational view of the medical instrument handled via a vertical pinch grip;

FIG. 10 is a side elevational view of the medical instrument handled via a horizontal pinch grip;

FIG. 11 is a side elevational view of the medical instrument handled via a syringe grip;

FIG. 12 is a side elevational view of the medical instrument handled via a palm grip;

Figure 1:
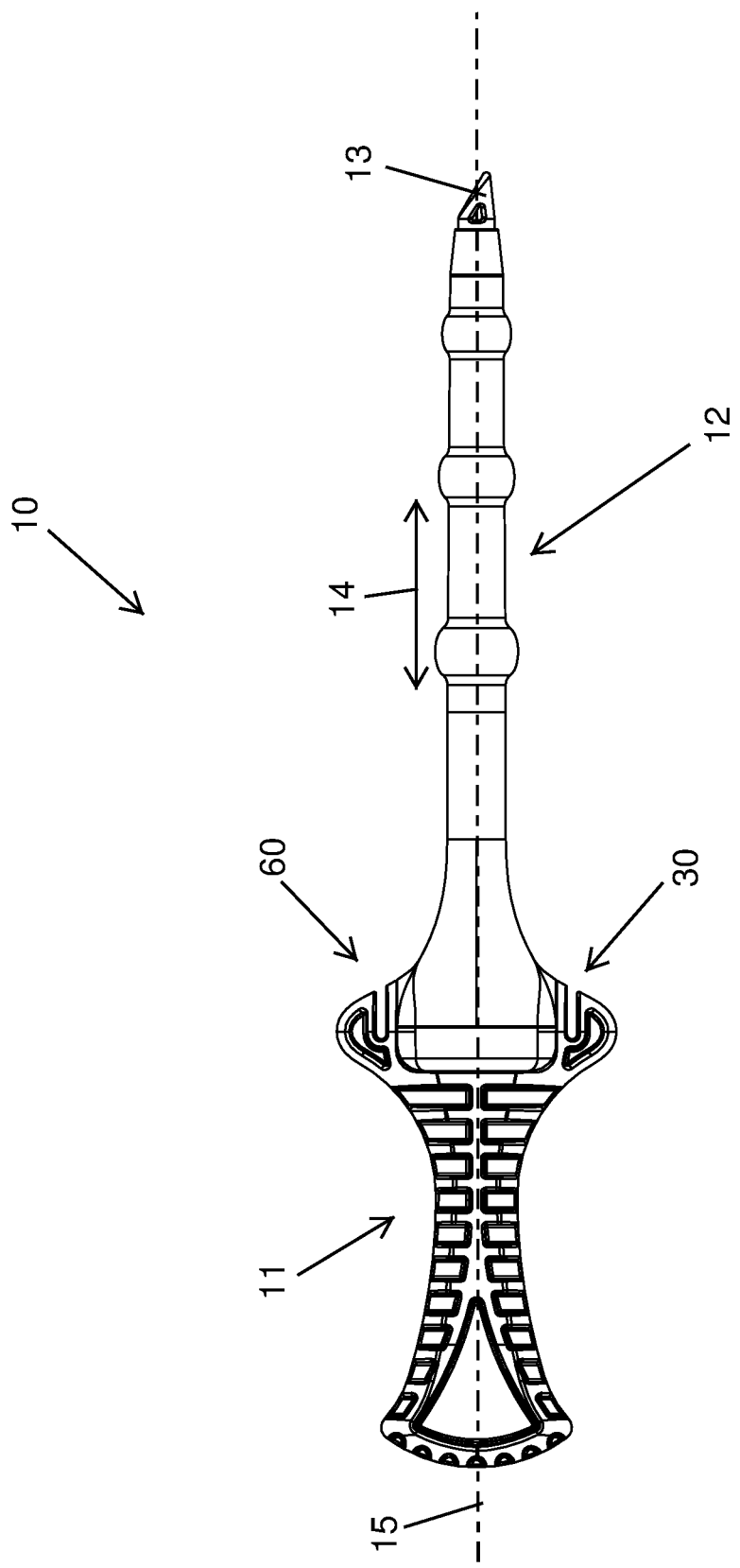
FIG. 1 is a side elevational view of a medical instrument (low profile, small cannula system), in accordance with a non-limiting exemplary embodiment.
Figure 2:
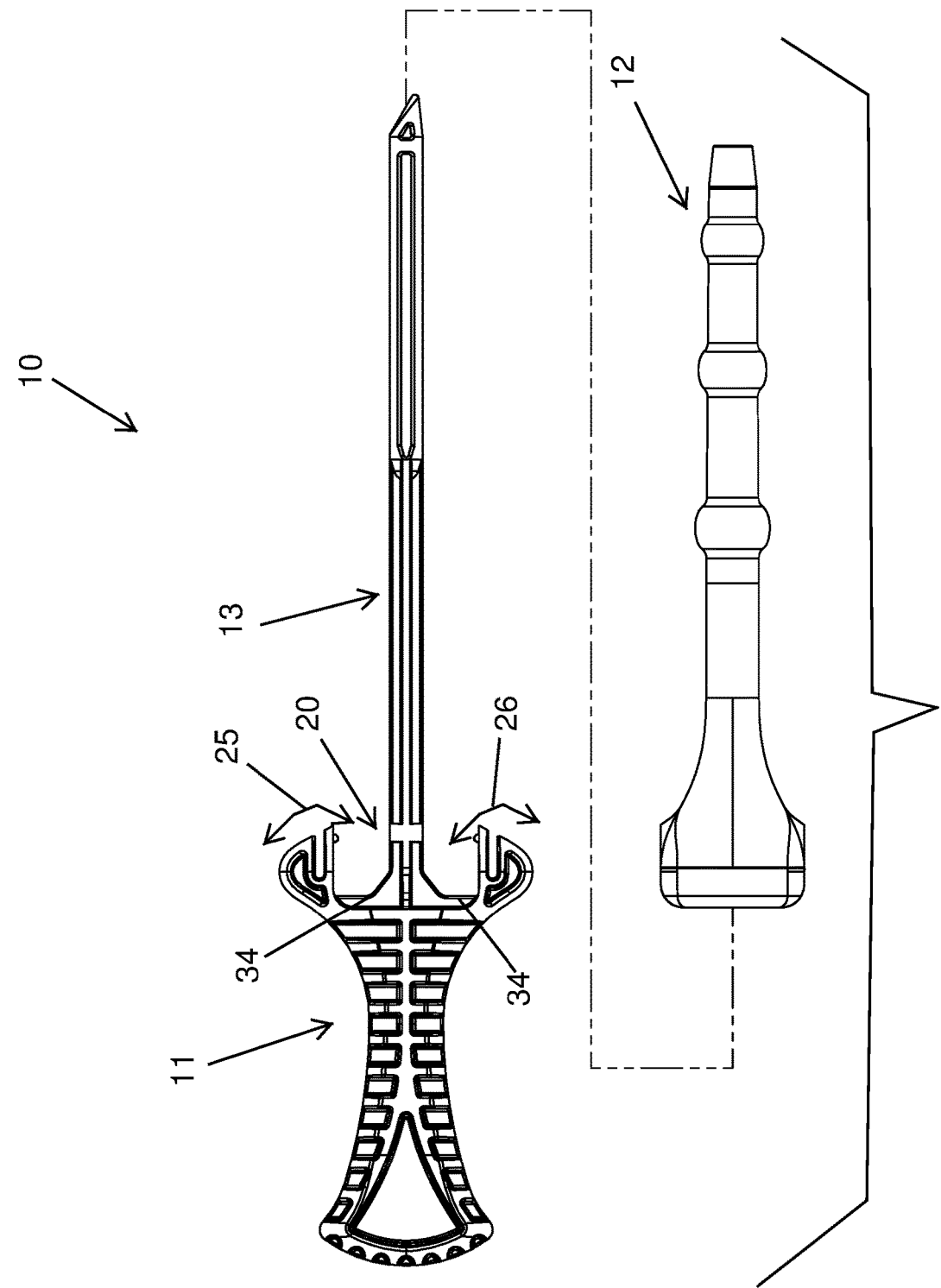
FIG. 2 is an exploded view of the medical instrument illustrated in FIG. 1.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

As used herein, "about" means approximately or nearly and in the context of a numerical value or range set forth means±15% of the numerical.

As used herein, "substantially" means largely if not wholly that which is specified but so close that the difference is insignificant.

As used herein, the term "proximal" refers to a location that, during normal use, is closer to the operator or clinician using the device and farther from the patient in connection with whom the device is used. Conversely, the term "distal" refers to a location that, during normal use, is farther from the clinician using the device and closer to the patient in connection with whom the device is used.

As used herein, the term "small cannula" refers to a cannula having a diameter less than about five millimeters, a preferably about 3 millimeters.

As used herein, the term "medical instrument" refers to non-limiting exemplary embodiments of a low profile, small cannula system.

The non-limiting exemplary embodiment(s) is/are referred to generally in FIGS. 1-20 and is/are intended to provide a low profile, small cannula system 10 employing fewer components, an ergonomic locking mechanism 60, cannula retention features 55, and a low profile multi-grip handle 11 for reducing manufacturing costs, minimizing undesirable movement during surgery, and facilitating desired manipulation of the cannula system 10. As noted hereinabove, such a low profile, small cannula system 10 is referred to as a "medical instrument" throughout the present disclosure.

The medical instrument 10 includes a handle 11, a trocar 13 in static communication with the handle 11, and a cannula 12 in dynamic communication with the trocar 13 and the handle 11. Notably, the cannula 12 is engaged with the handle 11 when linearly displaced proximally towards the handle 11 and, conversely, the cannula 12 is disengaged from the handle 11 when linearly displaced distally away from the handle 11. Advantageously, the cannula 12 is at a locked position 30 when linearly engaged with the handle 11 and the cannula 12 is at an unlocked position 31 when linearly disengaged from the handle 11. In this manner, the cannula 12 is linearly reciprocated, between the locked position 30 and the unlocked position 31, along a linear travel path 14 defined parallel to a longitudinal axis 15 of the trocar 13 such that the cannula 12 is prohibited and permitted to articulate (rotate) and translate (linearly travel) about the longitudinal axis 15 of the trocar 13, and relative to the handle 11, respectively.

Advantageously, the cannula 12 is locked and unlocked from the trocar 13 without requiring an external force to be exerted generally transverse to trocar 13 and/or cannula 12—thereby permitting a user to lock/unlock the cannula 12, relative to the trocar 13, with one hand.

In a non-limiting exemplary embodiment, the handle 11 includes a distal end 20 including a first locking flange 16 having a first male member 17 extending towards the linear travel path 14, and a second locking flange 18 having a second male member 19 spaced from the first male member 17 and extending towards the linear travel path 14. Notably, the cannula 12 is engaged and disengaged from each of the first male member 17 and the second male member 19 as the cannula 12 is linearly reciprocated (translated) along the linear travel path 14 towards and away from the distal end 20 of the handle 11, respectively. Again, no second external force (e.g., direct user force) generally transverse to the trocar 13 and/or cannula 12 (e.g., at first locking flange 16 and the second locking flange 18) is needed to lock/unlock the cannula 12. Advantageously, the user can perform such locking/unlocking functions with merely one hand.

In a non-limiting exemplary embodiment, the cannula 12 is caused to simultaneously engage and disengage each of the first male member 17 and the second male member 19 when the cannula 12 is linearly displaced between the locked position 30 and the unlocked position 31 30, respectively.

In a non-limiting exemplary embodiment, the cannula 12 includes a proximal end 21 including a perimeter outer wall 22 having a first female member 23 and a second female member 24 spaced therefrom. Such a first female member 23 and second female member 24 are aligned with the first male member 17 and the second male member 19, respectively, when the proximal end 21 of the cannula 12 is linearly introduced, along the longitudinal axis 15, into the distal end 20 of the handle 11. In this manner, the first male member 17 and the second male member 19 are operably received and retained within the first female member 23 and the second female member 24, respectively, as the proximal end 21 of the cannula 12 is linearly intercalated between the first locking flange 16 and the second locking flange 18. A suitable initial force of friction enables the cannula 12 to remain engaged with the trocar 11, when at the locked position 30.

Figure 3:
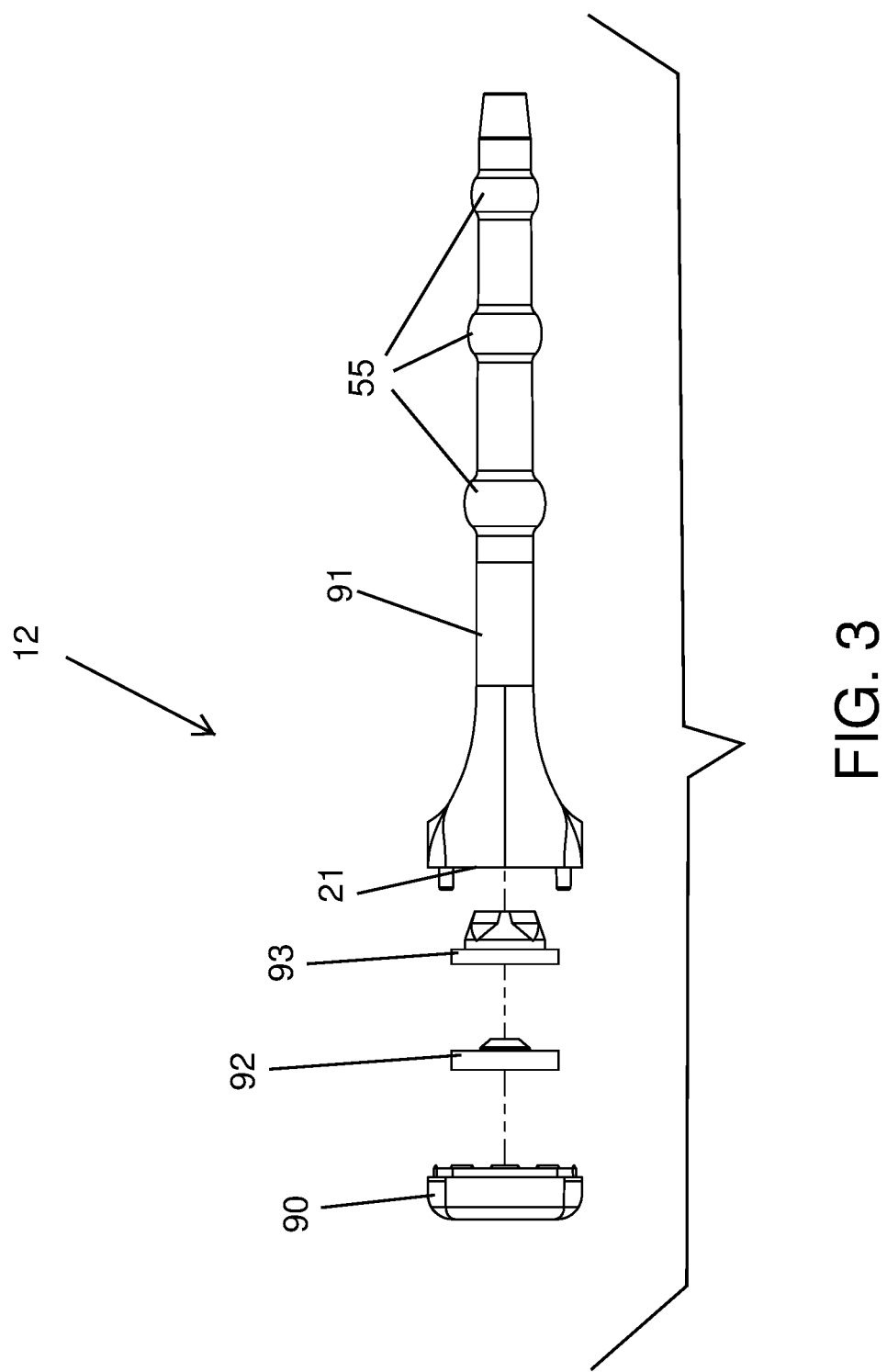
FIG. 3 is an exploded view of cannula illustrated in FIG. 2.
Figure 4:
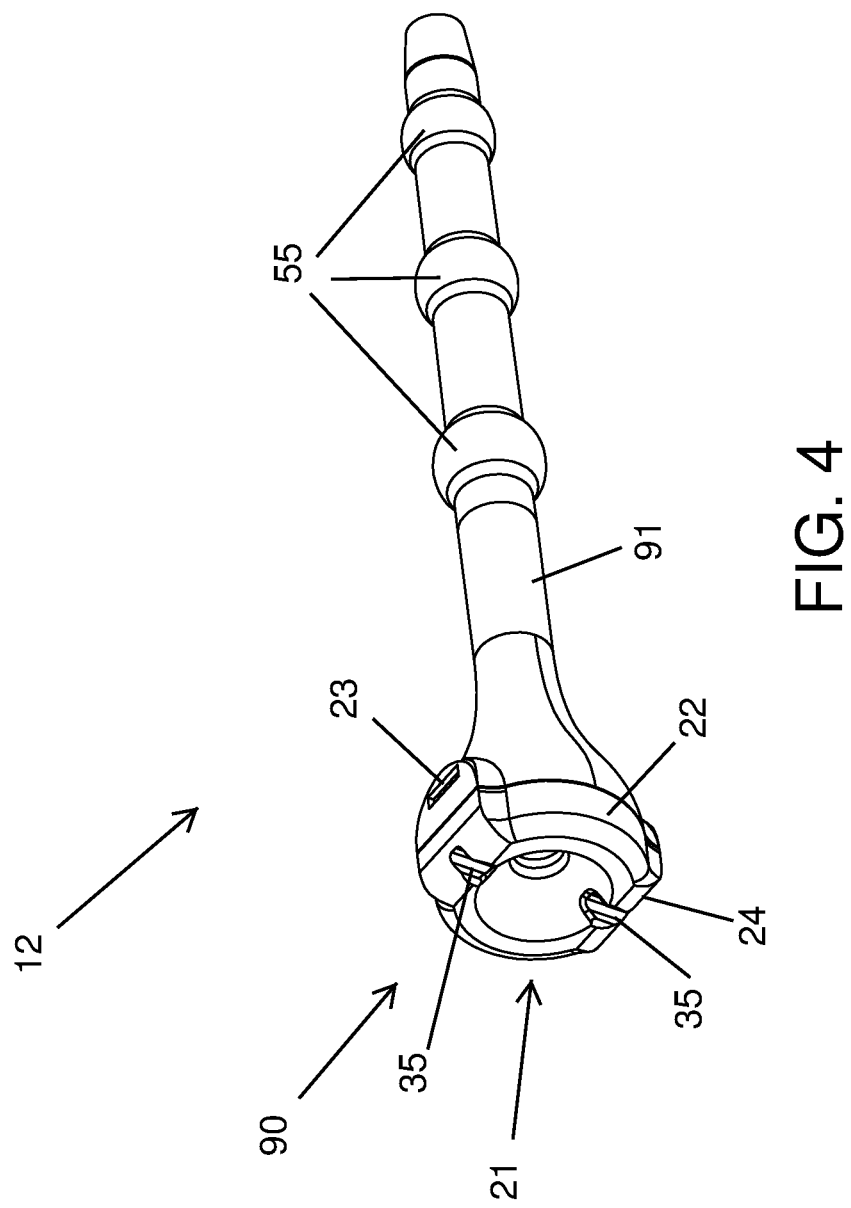
FIG. 4 is a perspective view of the cannula illustrated in FIG. 2.

As perhaps best shown in FIG. 3, the cannula 12 includes an end cap 90 connected to a proximal end 21 of the cannula shaft 91. A first seal 92 is abutted against an inner face of end cap 90. A second (backup) seal 93 is intercalated between the first seal 92 and the proximal end 21 of cannula shaft 91. Such a configuration requires minimal components and provides a secure mechanism for maintaining a peripheral medical implement at a substantially stable position relative to the cannula shaft 91 during surgical procedures.

In a non-limiting exemplary embodiment, each of the first locking flange 16 and the second locking flange 18 is caused to resiliently articulate along mutually exclusive arcuate paths 25, 26, respectively, away from and towards the linear travel path 14 as the cannula 12 is linearly reciprocated (translated) between the locked position 30 and the unlocked position 31 30, respectively. Such a structural configuration enables a practitioner to engage (lock) and disengage (unlock), with only one hand, the cannula 12 from the handle 11. Notably, the practitioner is not required to apply any external force against locking flanges 16, 18 when locking/unlocking the cannula 12 from handle 11. Rather, the practitioner need only apply a linear force along longitudinal axis 15 or travel path 14, for example. Such a single external force overcomes the initial force of friction for disengaging the handle 11 from cannula 12. This frees-up the practitioner's second hand during such locking/unlocking procedures.

Figure 8A:
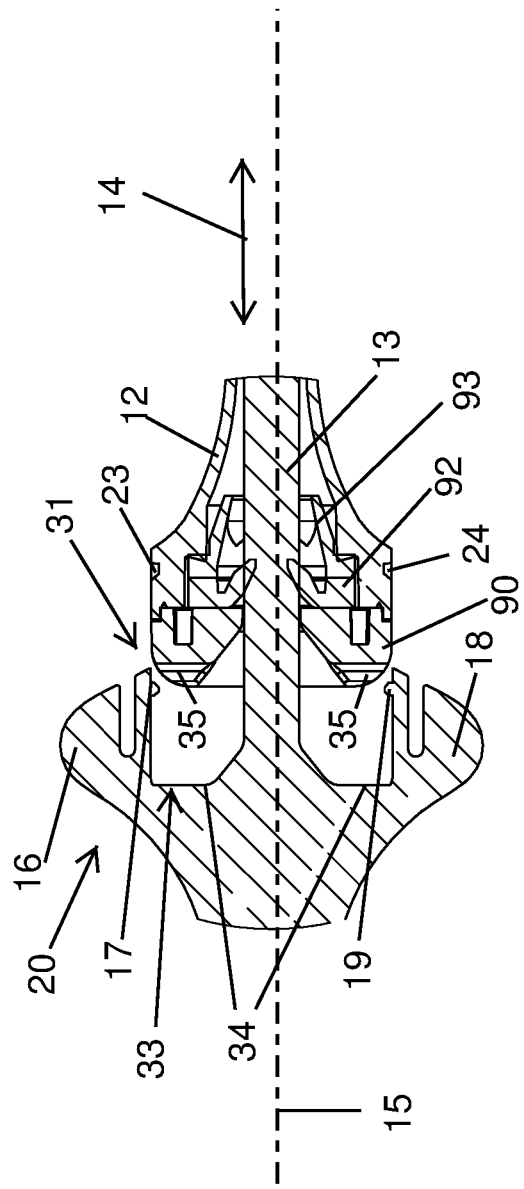
FIG. 8A is an enlarged view of section 8A identified in FIG. 8.
Figure 8:
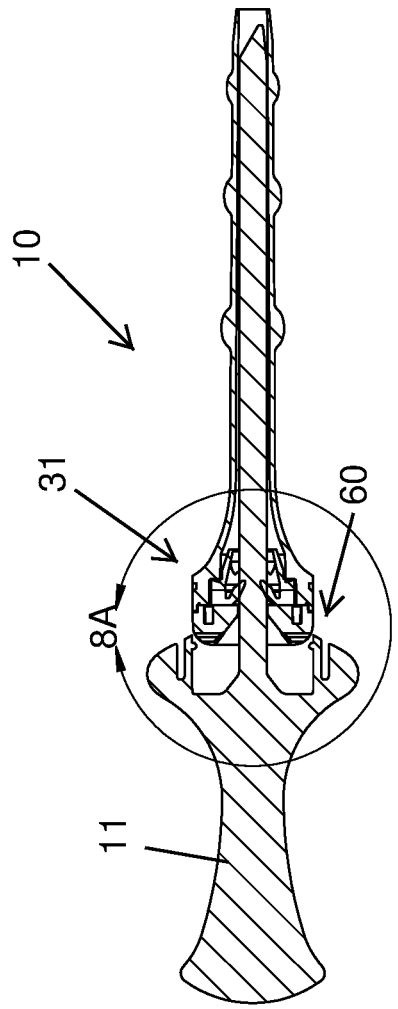
FIG. 8 is a cross-sectional view taken along line 8-8 in FIG. 7.
Figure 7:
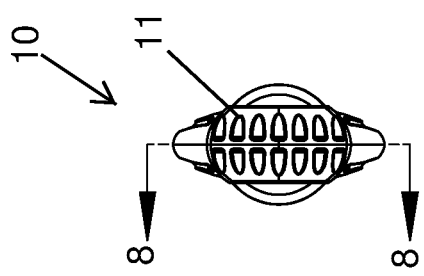
FIG. 7 is a rear elevational view of the medical instrument wherein the cannula is disengaged (unlocked) from the trocar.

In a non-limiting exemplary embodiment, the handle 11 further includes an inner wall 33 extending from the first male member 17 to the second male member 19, and at least one rib 34 intermediately disposed between the first male member 17 and the second male member 19. The at least one rib 34 is located on the handle inner wall 33 as best shown in FIG. 8A. Notably, the cannula 12 further includes at least one mating slot 35 (FIG. 8A) selectively engaged and disengaged with the at least one rib 34 when the cannula 12 is linearly reciprocated, along the linear travel path 14, between the locked position 30 and the unlocked position 31. Such a structural configuration prohibits the handle 11 and trocar 13 from undesirably rotating relative to cannula 11, during use.

In a non-limiting exemplary embodiment, the at least one rib 34 is linearly inserted and retracted from the at least one mating slot 35 so that the cannula 12 is prohibited and permitted to rotating about the longitudinal axis 15 of the trocar 13, and relative to the handle 11, when the cannula 12 is registered at the locked position 30 and the unlocked position 31 30, respectively. Advantageously, first locking flange 16 and the second locking flange 18 cooperate with the at least one rib 34 and the at least one mating slot 35, thereby serving to facilitate translation locking and rotation locking between the trocar 13 and cannula 12. The first locking flange 16 and the second locking flange 18 also provide grip support for the various grip positions, shown in FIGS. 9-12. Such a structural configuration enables a practitioner to engage (lock) and disengage (unlock), with only one hand, the cannula 12 from the handle 11. Notably, the practitioner is not required to apply any external force against locking flanges 16, 18 when locking/unlocking the cannula 12 from handle 11. This frees-up the practitioner's second hand during such locking/unlocking procedures.

In a non-limiting exemplary embodiment, the proximal end 21 of the cannula 12 has a proximal wall 32 linearly engaged and disengaged from the inner wall 33 of the handle 11 when cannula 12 is linearly reciprocated, along the longitudinal axis 15, between the locked positon and the unlocked position 30, 31, respectively.

In a non-limiting exemplary embodiment, as perhaps best shown in FIGS. 5-8A, the at least one of the first male member 17 and the second male member 19 includes a first engaging edge 50 and a first disengaging edge 51. Furthermore, at least one of the first female member 23 and the second female member 24 includes a second engaging edge 52 and a second disengaging edge 53. In this manner, when the at least one of the first male member 17 and the second male member 19 are seated within a corresponding one of the first female member 23 and the second female member 24, the first disengaging edge 51 lays substantially parallel to the second disengaging edge 53 and thereby maintains frictional contact therewith while the first engaging edge 50 lays non-parallel to the second engaging edge 52. Such a structural configuration enables a practitioner to engage (lock) and disengage (unlock), with only one hand, the cannula 12 from the handle 11. Notably, the practitioner is not required to apply any external force against locking flanges 16, 18 when locking/unlocking the cannula 12 from handle 11. This frees-up the practitioner's second hand during such locking/unlocking procedures.

In a non-limiting exemplary embodiment, the cannula 12 can also include the atraumatic retention features 55 disposed along the cannula 12 shaft for abdominal wall retention. Such retention features 55 may include spherical protrusions extending outwardly and about an outer wall of the cannula 12. The retention features 55 are preferably spaced along a longitudinal length of the cannula and are of suitable size and shape to provide friction surface contact with the abdominal wall opening at the incision site.

Referring to FIGS. 9-12, the handle 11 may be grasped via a variety of grips such as a vertical pinch grip 70, horizontal pinch grip 71, syringe grip 72, and palm grip 73. The low profile structure of handle 11 enables a practitioner to maneuver his/her grip during use of the system 10. Such maneuvering relieves stress and fatigue on the practitioner's metacarpals and allows for a variety of movements such as linear, arcuate, etc., during extended procedures and within space-limited working conditions.

Figure 13:
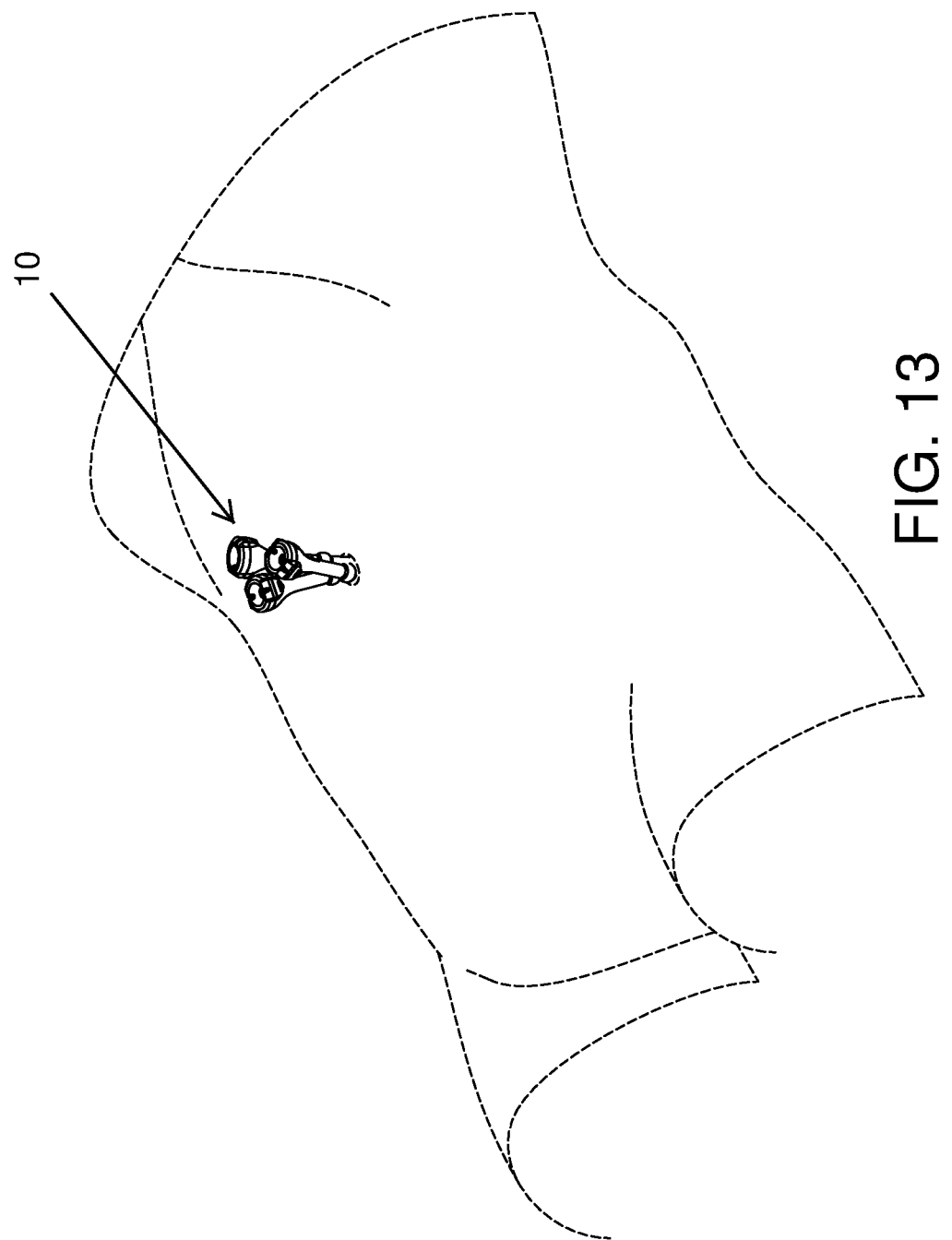
FIG. 13 is a perspective view of a cluster (e.g., side-by-side) of three medical instruments located at an exemplary environment.
Figure 14:
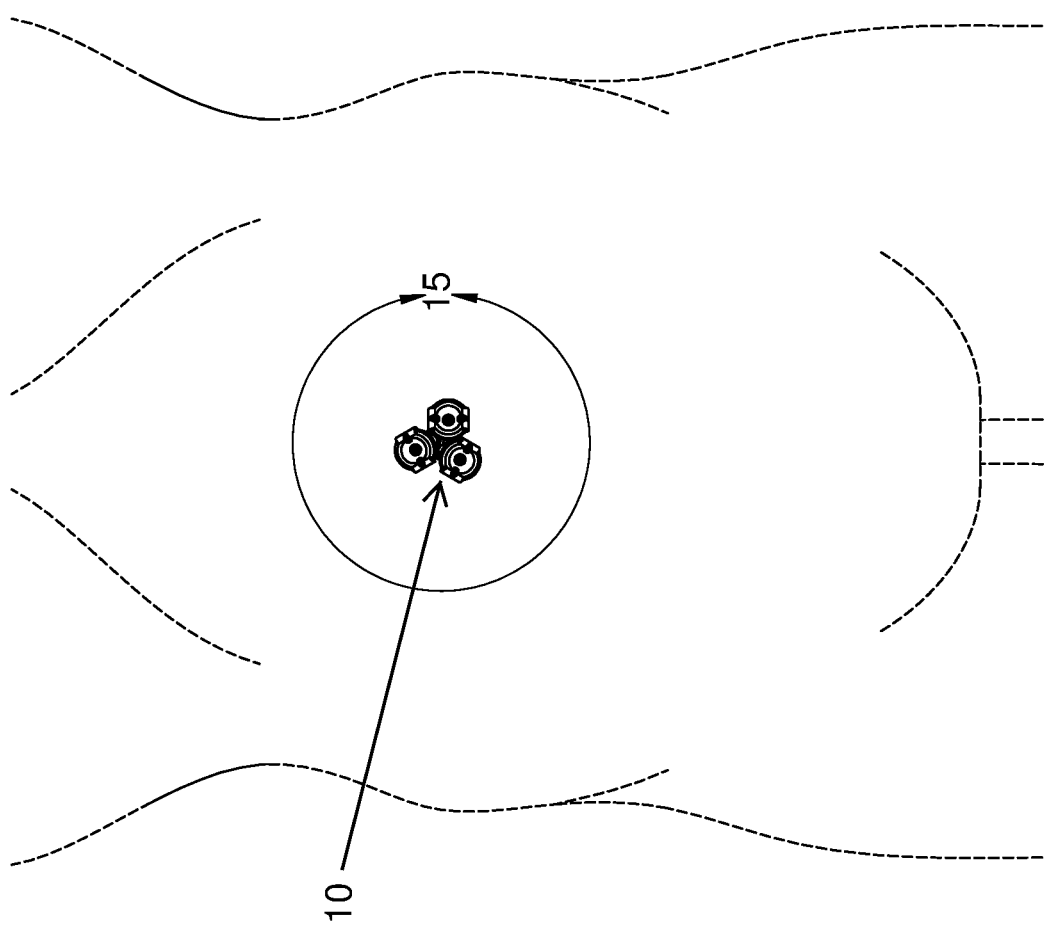
FIG. 14 is a top plan view of another cluster (e.g., side-by-side) of three medical instruments located at an exemplary environment.
Figure 15:
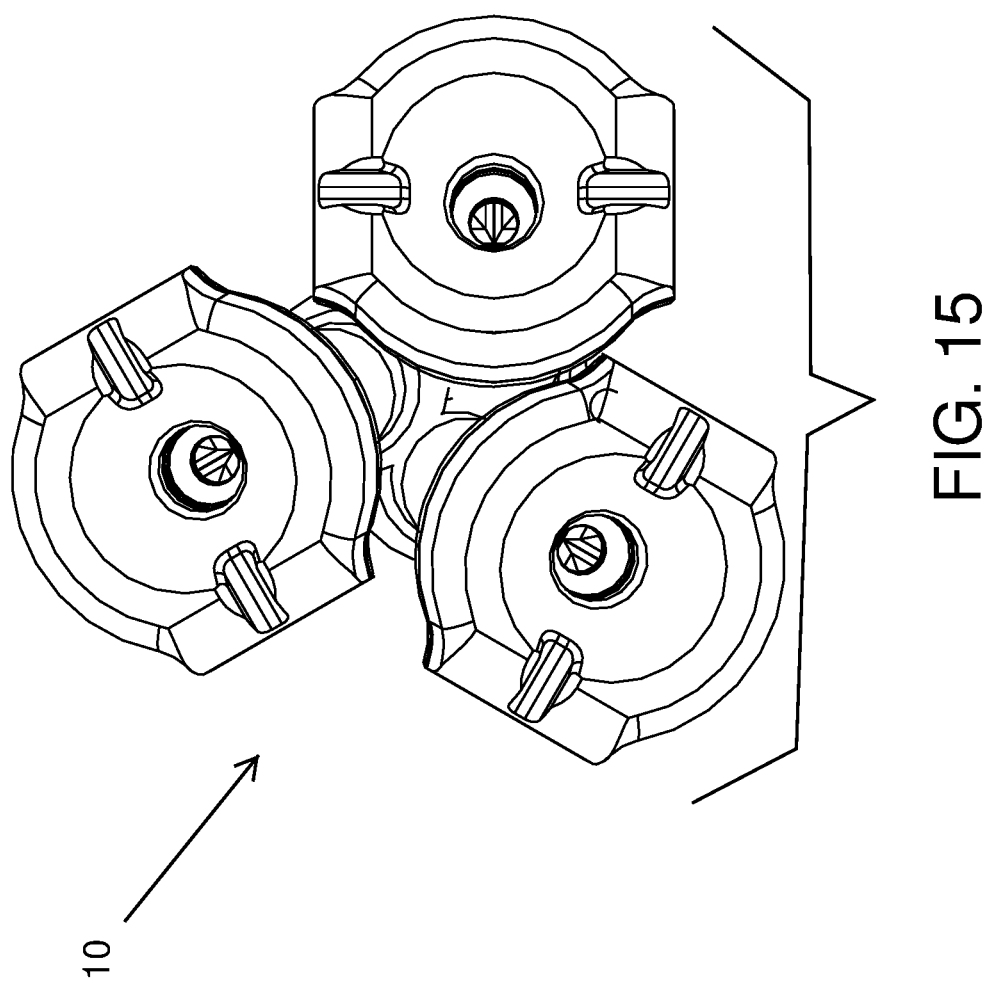
FIG. 15 is an enlarged top plan view of the cluster (e.g., side-by-side) of three medical instruments illustrated in FIG. 14.
Figure 16:
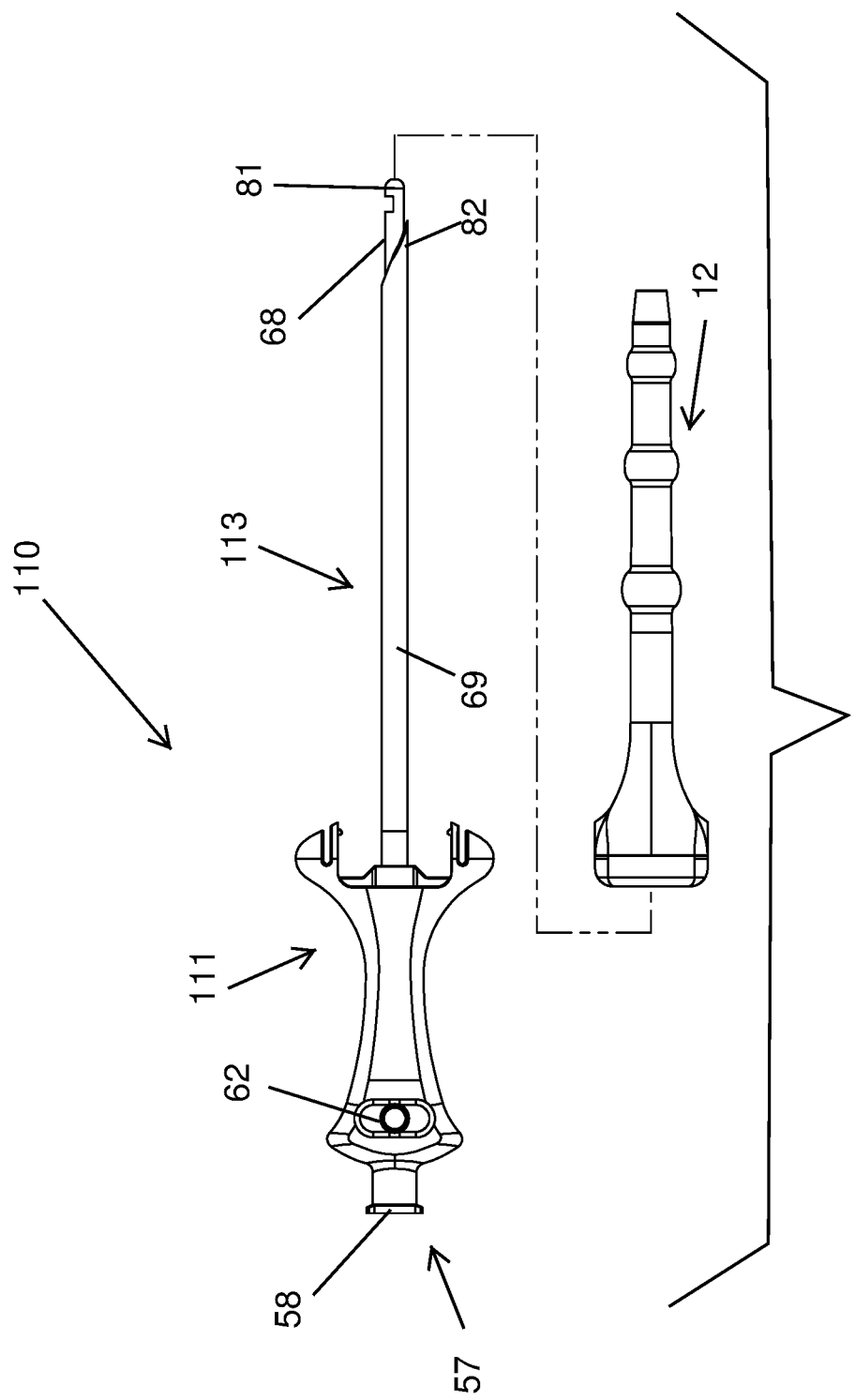
FIG. 16 is an exploded view illustrating another non-limiting exemplary embodiment of the present disclosure, wherein an insufflation port is employed at the cannula.
Figure 17:
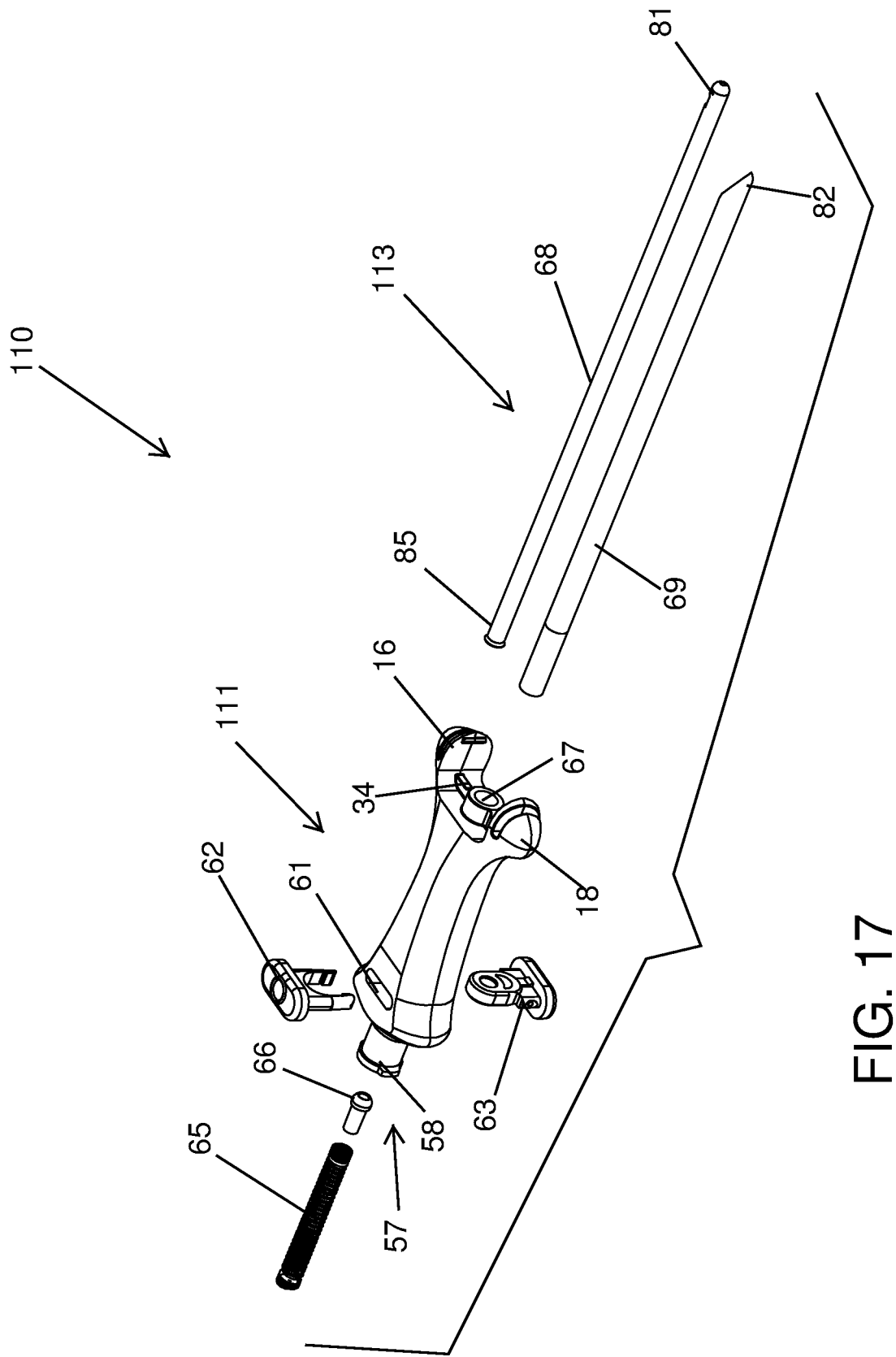
FIG. 17 is an exploded view of the trocar, handle and insufflation lock illustrated in FIG. 16.
Figure 18:
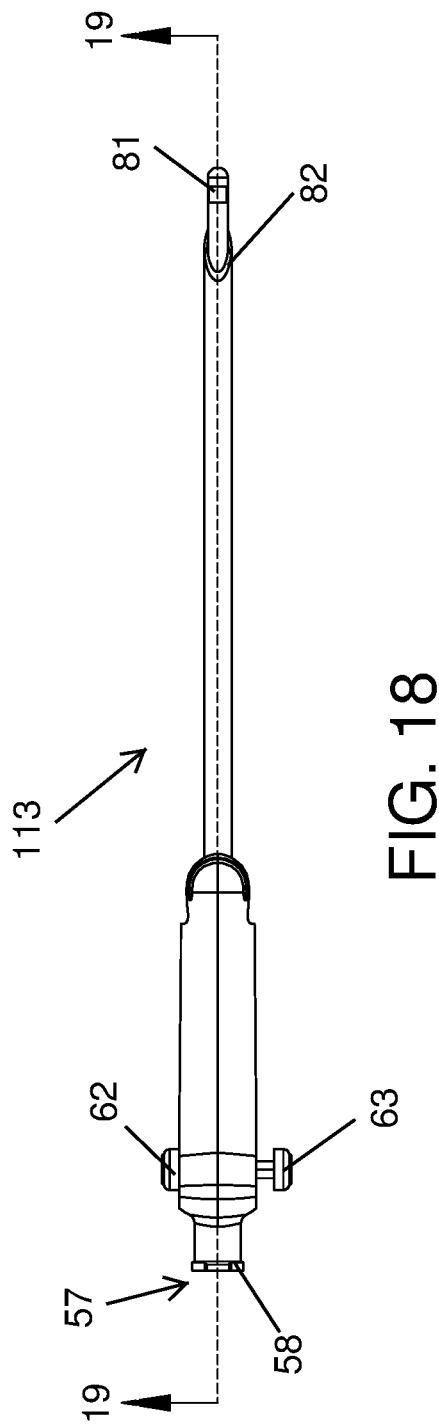
FIG. 18 is a top plan view of the handle, trocar and insufflation lock illustrated in FIG. 16.
Figure 19:
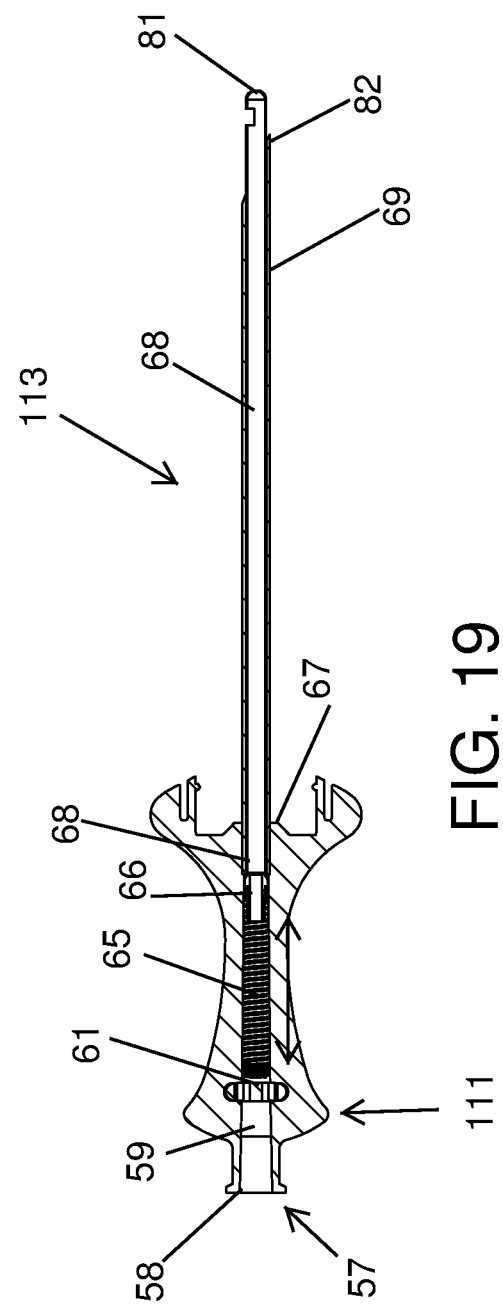
FIG. 19 is a cross-sectional view taken along line 19-19 in FIG. 18.

Referring to FIGS. 13-15, it can be seen that a cluster of low profile cannula systems 10 are positioned near each other, thereby enabling the practitioner to simultaneously employ a variety of medical implements (e.g., insufflation implement, cutting implements, endoscopic implement, etc.) at or near the same incision site.

Referring to FIGS. 16-19, a non-limiting exemplary embodiment 110 of the present disclosure is illustrated wherein the handle 111 includes an insufflation port 57 for introducing gas along the linear travel path 14, guided along cannula 12. The handle 111 includes an axial bore 59 aligned with a longitudinal axis of the trocar 113. A proximal end of the handle 111 is provided with a luer lock 58 for receiving and securely locking a peripheral device (e.g., gas-supplying source). A passageway 61 is formed transverse to the axial bore 59 for receiving a red slide valve 62 and a green slide valve 63 therethrough. The red slide valve 62 is engaged with the green slide valve 63 such that when the red slide valve 62 is pressed inwardly towards the axial bore 59, it pushes the green slide valve 63 outwardly away from the axial bore 59. This prohibits the peripheral device (e.g., gas-supplying source) from sending gas to the patient's incision site (e.g., stop gas flow). Conversely, pressing the green slide valve 63 inwardly towards the axial bore 59 causes the red slide valve 62 to egress outwardly way the axial bore 59. Such a configuration permits the peripheral device (e.g., gas-supplying source) to send gas to the patient's incision site (e.g., gas can flow).

A spring 65 and spring indicator 66 are seated within the axial bore 59 and intermediately confined between the insufflation lock 58 and an outlet port 67 located at a distal end of the handle 111. A proximal end 85 of a blunt stylus 68 is positioned through the outlet port 67 and mates with the spring indicator 66. A needle portion 69 of the trocar 113 receives the blunt stylus 68 therethrough such that the blunt stylus 68 is coaxially aligned within a hollow interior of the needle portion 69. In this manner, a distal tip 81 of the blunt stylus 68 sits exterior of the needle portion 69. Pressing trocar 113 against a patient's skin causes the blunt stylus 68 to distally retract within the needle portion 69 and thereby expose a sharp distal tip 82 of the needle portion 69 that penetrates through the patient's skin. Thus, the spring 65 is at a compressed and tensioned state. The spring 65 automatically returns to an uncompressed and non-tensioned state after the needle portion 69 penetrates the patient's skin, and thereby exposes the distal tip 81 of the blunt stylus 68 beyond the distal tip 82 of the needle portion 69.

Figure 20:
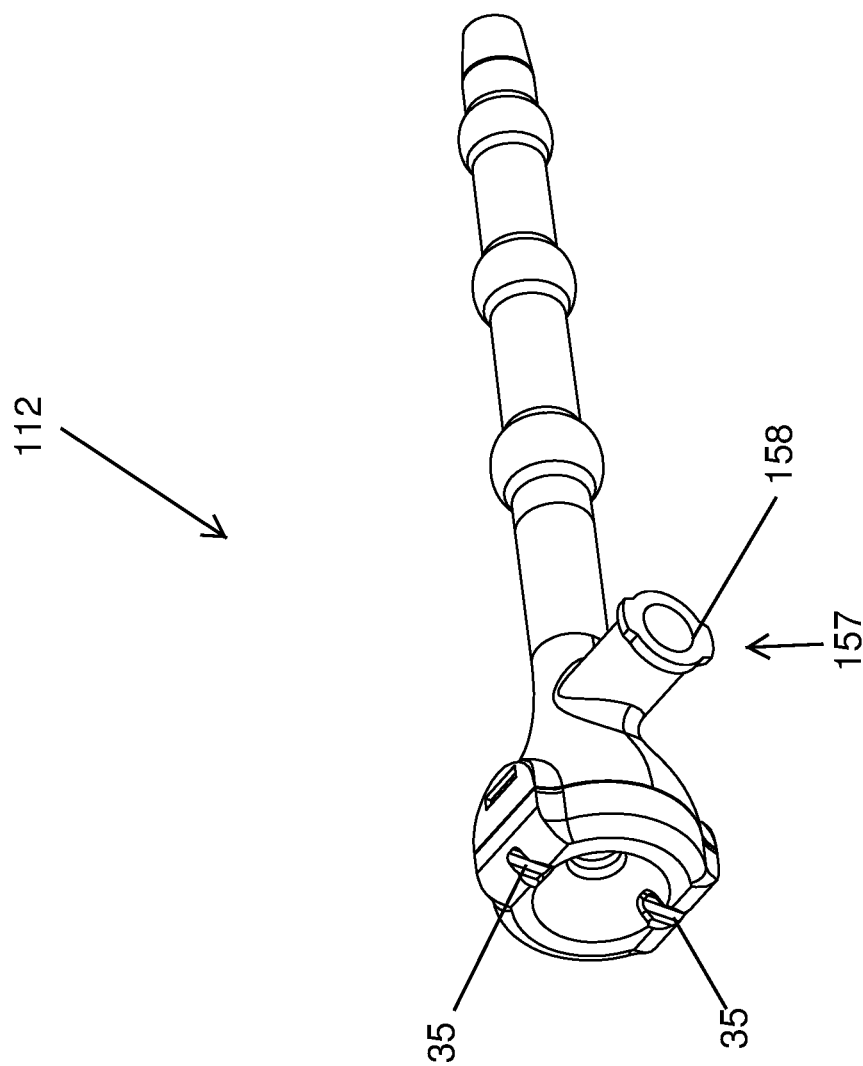
FIG. 20 is a perspective view of the cannula, employing an insufflation port, in accordance with yet another embodiment of the present disclosure.

With reference to FIG. 20, in a non-limiting exemplary embodiment, cannula 112 is provided with an insufflation port 157 and lock 158 for receiving and securely locking a peripheral device (e.g., gas supplying source), which may be used to introduce carbon dioxide, nitrogen or other suitable gases to a patient target zone (e.g., surgical site, etc.). Such a cannula 112 may be employed with alternate embodiments of the handle 11 and 111, as desired.

The present disclosure further includes a method for utilizing a medical instrument 10 during a medical procedure. Such a method includes the steps of: providing a handle 11; providing a trocar 13 in static communication with the handle 11; providing and dynamically communicating a cannula 12 with the trocar 13 and the handle 11; linearly engaging the cannula 12, at a locked position 30, with the handle 11 by linearly displacing the cannula 12 proximally towards the handle 11; linearly disengaging the cannula 12, to an unlocked position 31, from the handle 11 by linearly displacing the cannula 12 distally away from the handle 11; and prohibiting and permitting the cannula 12 to articulate about the longitudinal axis 15 of the trocar 13, and relative to the handle 11, respectively, by linearly reciprocating the cannula 12, between the locked position 30 and the unlocked position 31, along a linear travel path 14 defined parallel to a longitudinal axis 15 of the trocar 13.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the united states is:

1. A medical instrument for use during a medical procedure, said medical instrument comprising:
    a handle;
    a trocar in communication with said handle; and
    a cannula in selective communication with said trocar and said handle, said cannula being engaged with said handle when linearly displaced proximally towards said handle, said cannula being disengaged from said handle when linearly displaced distally away from said handle;
    wherein said cannula is at a locked position when linearly engaged with said handle and said cannula is at an unlocked position when linearly disengaged from said handle; said cannula being linearly reciprocated by a single user hand, between said locked position and said unlocked position, without exerting an external force generally transverse to said trocar and said cannula, along a linear travel path defined parallel to a longitudinal axis of said trocar such that said cannula is prohibited and permitted to articulate about said longitudinal axis of said trocar, and relative to said handle, respectively; and
    wherein said handle comprises a distal end including at least one locking flange with at least one male member which is caused to resiliently articulate along an arcuate path, away from and towards said linear travel path as said cannula is linearly reciprocated between said locked position and said unlocked position, respectively.

2. The medical instrument of claim 1, wherein said handle comprises:
    a first locking flange having a first male member extending towards said linear travel path; and
    a second locking flange having a second male member spaced from said first male member and extending towards said linear travel path; and
    said cannula being engaged and disengaged from each of said first male member and said second male member as said cannula is linearly reciprocated along said linear travel path towards and away from said distal end of said handle, respectively.

3. The medical instrument of claim 2, wherein said cannula is caused to simultaneously engage and disengage each of said first male member and said second male member when said cannula is linearly displaced between said locked position and said unlocked position, respectively.

4. The medical instrument of claim 2, wherein said cannula comprises: a proximal end including a perimeter outer wall having a first female member and a second female member spaced therefrom, said first female member and said second female member being aligned with said first male member and said second male member, respectively, when said proximal end of said cannula is linearly introduced, along said longitudinal axis, into said distal end of said handle; and
    said first male member and said second male member being operably received and retained within said first female member and said second female member, respectively, as said proximal end of said cannula is linearly intercalated between said first locking flange and said second locking flange.

5. The medical instrument of claim 4, wherein at least one of said first male member and said second male member comprises: a first engaging edge and a first disengaging edge;
    wherein at least one of said first female member and said second female member comprises: a second engaging edge and a second disengaging edge; and
    wherein, when said at least one of said first male member and said second male member is seated within a corresponding one of said first female member and said second female member, said first disengaging edge lays substantially parallel to said second disengaging edge and thereby maintains frictional contact therewith while said first engaging edge lays non-parallel to said second engaging edge.

6. The medical instrument of claim 2, wherein said handle further comprises:
    an inner wall extending from said first male member to said second male member; and
    at least one rib intermediately disposed between said first male member and said second male member; and
    wherein said cannula further comprises: at least one mating slot selectively engaged and disengaged with said at least one rib when said cannula is linearly reciprocated, along said linear travel path, between said locked position and said unlocked position.

7. The medical instrument of claim 6, wherein said at least one rib is linearly inserted and retracted from said at least one mating slot so that said cannula is prohibited and permitted to rotating about said longitudinal axis of said trocar, and relative to said handle, when said cannula is registered at said locked position and said unlocked position, respectively.

8. The medical instrument of claim 6, wherein a proximal end of said cannula has a proximal wall linearly engaged and disengaged from said inner wall of said handle when cannula is linearly reciprocated, along said longitudinal axis, between said locked position and said unlocked position, respectively.

9. The medical instrument of claim 1, wherein at least one of said handle and said cannula comprises: an insufflation port for introducing gas along said linear travel path.

10. A medical instrument for use during a medical procedure, said medical instrument comprising:
a handle;
a trocar in communication with said handle; and
a cannula in selective communication with said trocar and said handle, said cannula being engaged with said handle when linearly displaced proximally towards said handle, said cannula being disengaged from said handle when linearly displaced distally away from said handle;
wherein said cannula is at a locked position when linearly engaged with said handle and said cannula is at an unlocked position when linearly disengaged from said handle; said cannula being linearly reciprocated by a single user hand, between said locked position and said unlocked position, without exerting an external force generally transverse to said trocar and said cannula along a linear travel path defined parallel to a longitudinal axis of said trocar such that said cannula is prohibited and permitted to articulate about said longitudinal axis of said trocar, and relative to said handle, respectively;
wherein said handle comprises a distal end including a first locking flange having a first male member extending towards said linear travel path, and a second locking flange having a second male member spaced from said first male member and extending towards said linear travel path, wherein said cannula being engaged and disengaged from each of said first male member and said second male member as said cannula is linearly reciprocated along said linear travel path towards and away from said distal end of said handle, respectively; and
wherein each of said first locking flange and said second locking flange are caused to resiliently articulate along mutually exclusive arcuate paths, respectively, away from and towards said linear travel path as said cannula is linearly reciprocated between said locked position and said unlocked position, respectively.

11. A medical instrument for use during a medical procedure, said medical instrument comprising:
a handle;
a trocar in static communication with said handle; and
a cannula in dynamic communication with said trocar and said handle, said cannula being engaged with said handle when linearly displaced proximally towards said handle, said cannula being disengaged from said handle when linearly displaced distally away from said handle;
wherein said cannula is at a locked position when linearly engaged with said handle and said cannula is at an unlocked position when linearly disengaged from said handle; said cannula being linearly reciprocated, between said locked position and said unlocked position, along a linear travel path defined parallel to a longitudinal axis of said trocar such that said cannula is prohibited and permitted to articulate about said longitudinal axis of said trocar, and relative to said handle, respectively;
wherein said handle comprises a distal end including
a first locking flange having a first male member extending transverse to said linear travel path; and
a second locking flange having a second male member spaced from said first male member and extending transverse to said linear travel path; and
said cannula being engaged and disengaged from each of said first male member and said second male member as said cannula is linearly reciprocated by a single user hand along said linear travel path towards and away from said distal end of said handle, respectively, and without exerting an external force generally transverse towards the longitudinal axis and directly against each of said first locking flange and said second locking flange when locking and unlocking the cannula from said handle.

12. The medical instrument of claim 11, wherein said cannula is caused to simultaneously engage and disengage each of said first male member and said second male member when said cannula is linearly displaced between said locked position and said unlocked position, respectively.

13. The medical instrument of claim 11, wherein said cannula comprises: a proximal end including a perimeter outer wall having a first female member and a second female member spaced therefrom, said first female member and said second female member being aligned with said first male member and said second male member, respectively, when said proximal end of said cannula is linearly introduced, along said longitudinal axis, into said distal end of said handle; and
said first male member and said second male member being operably received and retained within said first female member and said second female member, respectively, as said proximal end of said cannula is linearly intercalated between said first locking flange and said second locking flange.

14. The medical instrument of claim 11, wherein each of said first locking flange and said second locking flange are caused to resiliently articulate along mutually exclusive arcuate paths, respectively, away from and towards said linear travel path as said cannula is linearly reciprocated between said locked position and said unlocked position, respectively.

15. The medical instrument of claim 11, wherein said handle further comprises:
an inner wall extending from said first male member to said second male member; and
at least one rib intermediately disposed between said first male member and said second male member; and
wherein said cannula further comprises: at least one mating slot selectively engaged and disengaged with said at least one rib when said cannula is linearly reciprocated, along said linear travel path, between said locked position and said unlocked position.

16. The medical instrument of claim 15, wherein said at least one rib is linearly inserted and retracted from said at least one mating slot so that said cannula is prohibited and permitted to rotating about said longitudinal axis of said trocar, and relative to said handle, when said cannula is registered at said locked position and said unlocked position, respectively.

17. The medical instrument of claim 15, wherein a proximal end of said cannula has a proximal wall linearly engaged and disengaged from said inner wall of said handle when cannula is linearly reciprocated, along said longitudinal axis, between said locked position and said unlocked position, respectively.

18. The medical instrument of claim 13, wherein at least one of said first male member and said second male member comprises: a first engaging edge and a first disengaging edge;

wherein at least one of said first female member and said second female member comprises: a second engaging edge and a second disengaging edge; and wherein, when said at least one of said first male member and said second male member is seated within a corresponding one of said first female member and said second female member, said first disengaging edge lays substantially parallel to said second disengaging edge and thereby maintains frictional contact therewith while said first engaging edge lays non-parallel to said second engaging edge.

\* \* \* \* \*